United States Patent [19]

Kientsch-Engel et al.

[11] Patent Number: 4,929,543
[45] Date of Patent: May 29, 1990

[54] PROCESS FOR THE DETERMINATION OF AN ANTIBODY IN HUMAN BODY FLUIDS

[75] Inventors: Rosemarie Kientsch-Engel, Pähl; Walter Wörner, Weilheim; Gerd Kleinhammer, Tutzing, all of Fed. Rep. of Germany

[73] Assignee: Boehringer Mannheim GmbH, Mannheim, Fed. Rep. of Germany

[21] Appl. No.: 192,957

[22] Filed: May 12, 1988

[30] Foreign Application Priority Data

May 14, 1987 [DE]  Fed. Rep. of Germany ....... 3716217
Jan. 4, 1988 [DE]  Fed. Rep. of Germany ....... 3800048

[51] Int. Cl.$^5$ ................. G01N 33/563; G01N 33/543; G01N 33/544; G01N 33/53
[52] U.S. Cl. ........................................ 435/5; 436/513; 436/518; 436/530; 436/819; 436/826; 436/512; 435/7
[58] Field of Search ............... 436/819, 826, 512, 518, 436/530; 435/7

[56] References Cited

U.S. PATENT DOCUMENTS 4,433,059  2/1984  Chang et al. ........................ 436/512

OTHER PUBLICATIONS

Klausner, A. Biotechnology, vol. 5, pp. 867–868, Sep. 1987.
Marx, J. Science, vol. 229, pp. 455–456, Aug. 1985.
Tijssen, P., In Practice and Theory of Enzyme Immunoassays pub. Elsevier, Amsterdam, 1985, vol. 15, Chapter 14, pp. 330–336.

Primary Examiner—Christine M. Nucker
Assistant Examiner—Karen I. Krupen
Attorney, Agent, or Firm—Felfe & Lynch

[57] ABSTRACT

The present invention provides a process for the determination of an antibody in human body fluids according to the immunoassay principle in which a sample containing the antibody to be determined is incubated with at least two different receptors $R_1$ and $R_2$, of which one receptor $R_1$ carries an antigenic determinant specific for the antibody to be determined and one receptor $R_2$ carries a label to form bound and unbound label, the part which contains the bound label is separated from the part which contains the unbound label and the label is measured in one of the two parts, wherein, for the control, instead of the sample, there is used a standard solution which contains a conjugate of a bindable non-human antibody or a Fab or F(ab')$_2$ fragment thereof which non-human component binds with a receptor $R_s$ which also binds to the antibody to be determined, and a human immunoglobulin or the Fc part thereof. The present invention also provides a control reagent for the determination of an antibody in human body fluids according to the immunoassay principle, containing a conjugate of an antibody bindable with the receptor $R_s$ specific for the antibody to be determined or a Fab or F(ab')$_2$ fragment thereof with a human immunoglobulin or the Fc part thereof, and said receptor.

14 Claims, No Drawings

PROCESS FOR THE DETERMINATION OF AN ANTIBODY IN HUMAN BODY FLUIDS

The present invention is concerned with a process and a control reagent for the determination of an antibody in human body fluids.

More particularly, the present invention is concerned with a process for the determination of an antibody in human body fluids, in which a sample containing an antibody to be determined is incubated with at least two different receptors $R_1$ and $R_2$, wherein receptor $R_1$ carries a specific antigenic determinant for the antibody to be determined and one receptor $R_2$ carries a label, the part which carries the bound label is separated from the part which carries the unbound label and the label is measured in one of the two parts. The present invention is also concerned with a control reagent for carrying out this process.

The determination of antibodies present in body fluids is often desirable. For example, the detection of certain antibodies gives an indication as to whether an infection has taken place or whether an allergy exists. This is important, for example, when it is to be ascertained whether an allergically-caused shock is to be anticipated in the case of the administration of a medicament. Furthermore, an auto-immune disease can be diagnosed by the detection of auto-immune antibodies. The detection of antibodies formed by therapy with, for example, medicaments which contain recombinant proteins, such as insulin and erythropoietin, for example, anti-insulin antibodies, is also of importance.

Since the antibodies are present in blood in very small amounts, very sensitive processes are necessary for their detection. Therefore, a process according to the immunoassay principle is indicated. One advantage of this method of determination is its precision and the possibility of being able to detect very small amounts of substances.

Various variants on general immunoassay processes are possible for carrying out the determination of antibodies in both homogeneous and in heterogeneous phases. In the case of heterogeneous phase assays, one of the receptors is bound to a carrier. For example, in the case of the so-called sandwich process, a receptor carrying an antigenic determinant specific for the antibody to be determined is bound to a carrier and is added to the test solution, the antibody to be determined contained in the test solution thereby being bound to the receptor. Labelled receptor is then added thereto which reacts specifically with the antibody or with the antigen-antibody complex. The amount of antibody in the sample can then be determined via the labelled receptor. There are many possible variations on this general principle. For example, determination can take place with three receptors, one of the three receptors being in solid phase and the other two receptors being soluble, one of the two soluble receptors being labelled, whereas the other one is unlabelled. The insoluble receptor is then directed against the unlabelled soluble receptor.

Determination of antibodies to insulin traditionally takes place with a radio-immunoassay. The patient sample is incubated with iodine-labelled insulin, to form bound, radioactive insulin. This is then precipitated out of the sample, either with polyethylene glycol or with a second antibody against human immunoglobulin and the radioactivity of the precipitate is determined. Recently, methods of determination following enzyme immunoassay principles (see T. J. Wilkin (1986), "The measurement of insulin antibodies and its interpretation", in Immunoassay Technology, Vol. 2 (ed. S. B. Pal), W. de Gruyter, Berlin) have been described.

A disadvantage of this known process is that test results which have been obtained on different days in the case of different reaction times with the substrate or under different reaction conditions, cannot be compared. Therefore, it has already been suggested that a sample of patient serum which is known to contain an antibody against insulin or which has been isolated from a positive patient's serum, be co-determined as an internal standard (see B. M. Dean, et al., Diabetologia 29, 339-342/1986; Nell, et al., Diabetes, 34, 60-66/1985). The test of the known positive serum also serves as a function control for all reagents used for the test. However, a problem in the case of using positive patients' serum is that not every laboratory has access to appropriate patients' sera and these patients' sera are also not available in sufficient amount. Furthermore, there is also the danger that patients' sera can be infectious. It can contain, for example hepatitis or HIV viruses. In addition, there are great variations from one patient to another so that test results with standard sera from different patients are not comparable. Even in the case of sera which have been taken from the same patient at different times, differing antibody titres can be expected. It is not possible to compare values which have been obtained from different laboratories.

Therefore, it is an object of the present invention to provide a process which permits one to provide a control value for processes for detection of antibodies and which, in addition, permits comparison of test results.

Thus, the present invention provides a process for the determination of an antibody in human body fluids according to the immunoassay principle comprising incubating a sample containing an antibody to be determined with at least two different receptors $R_1$ and $R_2$, wherein one receptor $R_1$ carries an antigenic determinant specific for the antibody to be determined and one receptor $R_2$ carries a label, separating bound label from unbound label and measuring the label in one of the two parts (i.e., the bound or unbound part) and comparing the measurement obtained to a control, said control being obtained by incubating a conjugate of a non-human antibody, (OR F(ab')$_2$ thereof and a human immunoglobulin or Fc portion thereof which conjugate binds to the same receptor as the antibody to be determined and the receptors with which said sample is incubated.

Surprisingly, we have ascertained that a chemically synthesized conjugate of an antibody which is bindable with the epitope specific for the antibody to be determined and with a non-specific human immunoglobulin reacts in the same way as the corresponding antibody from the patients' samples. The non-human antibody part of the conjugate thereby provides the specific reaction with a receptor "$R_s$", whereas the human immunoglobulin portion ensures detectability of the conjugate. The conjugate used according to the present invention is available in unlimited amounts and can always be prepared.

Processes for the determination of an antibody in human body fluids according to the immunoassay principles are known. These processes are used, on the one hand, in order to detect antibodies formed against bacteria or viruses. In this way, an infection which has already taken place or the course thereof can be monitored. Examples of this include antibodies against hepatitis viruses and against HIV. These processes can also be used in order to detect auto-antibodies. Auto-antibodies are antibodies directed against the body's own antigens which are formed in the case of an auto-immune disease. Detection of auto-antibodies permits diagnosis of the disease. Examples include thyroid antibodies and the auto-antibodies against inherent insulin or against islet cells of the pancreas which probably arise in conjunction with the appearance of diabetes mellitus. The detection of insulin antibodies which are formed in the case of human diabetic patients who have been treated with animal insulin is also important. Since insulin does not differ very much from species to species, it results in strong cross-reactions so that, due to antibodies against any insulin, the insulin in the serum is neutralized and can possibly even given rise to insulin resistance. In the case of treatment with recombinant proteins, for example erythropoietin or plasminogen activators, the formation of antibodies against these proteins can be anticipated and thus must also be tested for. Also of interest for the diagnosis of allergies is the detection of antibodies specific for particular allergens.

Many variants are possible for carrying out the process for the determination of an antibody. A widely used variant is the sandwich assay in which a receptor $R_1$ is present bound to a solid phase, whereas another receptor $R_2$, which carries a label, is soluble. There are further variants with two soluble receptors $R_1$ and $R_2$ or with one bound receptor $R_1$ and two soluble receptors, one of which, $R_2$, carries a label. The process according to the present invention can be used for all of these variants.

As receptors $R_1$ and $R_2$, there can be used, for example, substances which carry an epitope specific for the antibody to be determined. These can be antigens, antigen fragments, anti-idiotype antibodies or haptens. The antibody-specific substances contained in the receptors $R_1$ and $R_2$ can be the same or different.

The labelling of a receptor is itself known. Usually enzymes, radio-active substances or fluorescing or chemiluminescing substances are used. The detection then takes place in known manner by measurement of the radio-activity, chemiluminescence or fluorescence or by the enzyme reaction with an appropriate colored substrate.

By receptors $R_s$ are to be understood substances which carry at least one epitope specific for the antibody to be determined, for example antigens, antigen fragments, anti-idiotypic antibodies or haptens. The antibodies or antibody fragments bindable with this receptor $R_s$ used according to the present invention also include conjugates of antibodies or antibody fragments with haptens.

In carrying out an immunoassay for the determination of an antibody, according to the present invention, a control assay is also carried out at the same time as the assay, which is used as an internal standard. Furthermore, this control serves as a function control for all reagents used in the test. For this purpose, instead of the sample, a standard solution which contains the aforementioned conjugate, the conjugate containing a non-human antibody is used. All combinations between the two components and fragments thereof are possible as members of the conjugate.

The conjugate is prepared by covalent binding of the two components, i.e. non-human antibody and human immunoglobulin or fragments thereof. Processes for the covalent binding of proteins are well known. A number of processes are described, for example, in P. Tijssen, Practice and Theory of Enzyme Immunoassays, pub. Elsevier, Amsterdam, 1985, Chapter 11. These processes are well suited for the preparation of the conjugates used according to the present invention with the use of homobifunctional or heterobifunctional reagents as cross-linking agents.

For the preparation of the conjugate, preferably a thiol group is introduced into one of the two components and a maleimide group into the other. The conjugation of the two is achieved by covalent binding of the thiol component with the maleimide group.

As antibodies, there can be used not only polyclonal but also monoclonal antibodies which are bindable with the specific antigenic determinants for the antibodies to be determined. Preferably, however, monoclonal antibodies are used from an animal which produces antibodies upon immunization with the antigenic determinants. As animal species, examples include the guinea pig, mice and rats, antibodies from the latter two being preferred. The antibody to be determined can originate from various antibody classes. IgG, for example, can be used in the case of diagnosis of infections; IgM in the case of the early state of an infection; IgA in the case of the detection of special infections, for example infections with the Epstein-Barr virus, and IgE which occurs in the case of allergies.

Furthermore, the present invention also provides a control reagent for the determination of an antibody in human body fluids, containing a conjugate of an antibody bindable with the specific antigenic determinant for the antibody to be determined or a Fab or F(ab')$_2$ fragment thereof with a human immunoglobulin or the Fc part thereof, and at least one receptor "$R_s$", which specifically binds both with the conjugate and the antibody to be determined.

The control reagent according to the present invention is prepared for the particular special immunoassay. In each case, specifically for each test, an antibody or the Fab or F(ab')$_2$ fragment thereof is conjugated with a human immunoglobulin or the Fc part thereof. In order to achieve the greatest possible comparability with the unknown serum samples, the control reagent is preferably dissolved in normal serum which possibly also contains detergents. However, dissolution in serum-free buffer is also possible.

According to the present invention, there is provided a process and a control reagent for the determination of an antibody in body fluids which makes it possible to compare test results with one another and to carry out simultaneously internal standards for increasing the exactitude of the measurement. The conjugate used according to the present invention can be reproduced in unlimited amounts.

The following Examples are given for the purpose of illustrating the present invention.

EXAMPLE 1

Preparation of a conjugate from mouse monoclonal antibody against insulinand human immune-γ-globulin.

In order to cross-link the two components, i.e. mouse insulin antibody and immune-γ-globulin, a thiol group was introduced into the antibody and a maleimide group into the immune-γ-globulin. The introduction of the thiol group into the mouse antibody was carried out substantially in the manner described by Klotz and Heiney (Arch. Biochem. Biophys., 96, 605-612/1962). For this purpose, 10 mg of mouse anti-insulin antibody (ATCC HB 123) were dissolved in 1 ml of a 0.1M potassium phosphate solution with a pH of 8.2 which contained 150 mM sodium chloride. 20 µl S-acetylmercaptosuccinic anhydride (43.6 mg/ml dimethyl sulphoxide) were added to the above solution and left to react for 1 hour at 25° C. Subsequently, the reaction mixture was dialyzed at 4° C. against 0.1M potassium phosphate (pH 6.2) which contained 1 mM ethylenediaminetetraacetic acid (EDTA).

30 mg human immune-γ-globulin were dissolved in 1 ml of a 30 mM sodium phosphate solution with a pH of 7. 20 µl Maleimidohexanoyl-N-hydroxysuccinimide ester (18.4 mg/ml dimethyl sulphoxide) were added thereto and left to react for one hour at 25° C. The solution was then applied to an Ultrogel AcA 202 column and the fractions which contained the protein were collected.

6 mg of the acetylmercaptosuccinylated mouse antibody and 18 mg of the maleimide human immune-γ-globulin were incubated in a volume of 5 ml of 0.1M potassium phosphate solution with a pH of 7.0 which contained 1 mM EDTA and 20 mM hydroxylamine, the hydroxylamine serving to activate the thiol group by cleavage of the thiol ester bond. The reaction mixture was incubated for two hours at 25° C. The incubation mixture was concentrated to 1 ml by ultrafiltration and applied to a Sephacryl-S-300 column (1.5×50 cm) and equilibrated with 50 mM sodium phosphate containing 150 mM sodium chloride and 0.1% sodium azide. The fractions which eluted before the monomeric immune-γ-globulins were collected and contained the conjugate of mouse anti-insulin antibody and human immune-γ-globulin.

EXAMPLE 2

The carrying out of the antibody determination took place essentially in the manner described by Dean et al. (Diabetologia, 29, 339-342/1986).

For the preparation of insulin-coated plates, human insulin (1 µg/ml) was dissolved in 50 mM sodium carbonate buffer with a pH of 9.6. The coating (125 µl per well) took place over the course of 5 hours at 20° C. in flat-bottomed microtitre plates (Nunc Immunoplate I). Thereafter, the plates were tipped out, tapped out on to cellulose and recoated overnight at 20° C. with 20% (v/v) goat normal serum in phosphate buffered saline (PBS). The recoating solution was tipped out, the plates were thoroughly tapped out on blotting paper, dried overnight at ambient temperature, subsequently sealed with adhesive film and stored at −20° C. until used.

An immunoassay was then carried out with these plates. The sample incubation thereby took place in 10% (v/v) goat normal serum/5% (v/v) Tween 20 in PBS for 1.5 hours at ambient temperature with continuous shaking (300 rpm). The appropriate sample dilution was incubated as double value (100 µl per well). After 1.5 h the solution was sucked out and the plkate was washed three times with, in each case, 300 µl wash medium per well (0.1% (v/v) Tween 20 in PBS) with standing times of 1/3/3 minutes.

The bound insulin antibody molecules were detected with a second antibody from sheep which was directed against the Fcγ-part of the human immunoglobulin molecule and which was, in turn, labelled with peroxidase. The second immune reaction lasted for one hour (also with shaking at 300 rpm) and was concluded with a washing step as described above.

The indicator reaction of the peroxidase took place in citrate buffer (pH 4.5), in which the peroxidase reacted with sodium perborate and ABTS® and the color development was measured at given times on an ELISA photometer at 405 nm subtracting the reference signal at wavelength λ=490 nm) with ABTS® as blank.

The following Table I shows the sample evaluation at different times after the commencement of the substrate reaction. It was found that the ratio of the measurement values of sample and function control remained constant during the whole of the substrate reaction time. Thus, the substrate reaction can be measured at any desired time after the commencement of the substrate reaction.

ABTSR 2,2'- Azino-di-[3-ethyl-benzthiazolin-sulfonic-acid(6)]-diammonium salt

TABLE I

Sample evaluation after different substrate reaction times (measurement wavelength 405 nm)

| sample | substrate reaction (min.) | | | | | | | |
|---|---|---|---|---|---|---|---|---|
| | 15 | | 30 | | 45 | | 60 | |
| | ΔE | % | ΔE | % | ΔE | % | ΔE | % |
| MAB <insulin>-H-IgG (1:30) | 0.576 | 100 | 0.962 | 100 | 1.276 | 100 | 1.534 | 100 |
| 1 | 0.057 | 9.9 | 0.097 | 10.1 | 0.122 | 9.6 | 0.151 | 9.8 |
| 2 | 0.155 | 26.9 | 0.261 | 27.1 | 0.349 | 27.4 | 0.427 | 27.8 |
| 3 | 0.330 | 57.3 | 0.560 | 58.2 | 0.756 | 59.2 | 0.902 | 58.8 |
| 4 | 0.338 | 58.7 | 0.570 | 59.3 | 0.776 | 60.8 | 0.946 | 61.7 |
| 5 | 0.506 | 87.8 | 0.849 | 88.3 | 1.127 | 88.3 | 1.369 | 89.2 |

The following Table II shows the sample evaluation on different days. Here, too, it was shown that, in spite of a different ΔE value for the function control, the ratio of the measurement value of sample and function control remained constant.

TABLE II

| day | MAB <ins>-H-IgG | | sample | | |
|---|---|---|---|---|---|
| | ΔE | % | 1 % | 2 % | 3 % |
| 1 | 1.235 | 100 | 33.7 | 32.5 | 64.7 |
| 2 | 1.237 | 100 | 39.0 | 33.6 | 67.7 |
| 3 | 1.268 | 100 | 39.4 | 30.5 | 67.5 |
| 4 | 1.280 | 100 | 33.4 | 30.9 | 63.8 |
| 5 | 1.327 | 100 | 40.2 | 29.9 | 65.2 |
| 6 | 1.350 | 100 | 36.1 | 34.7 | 68.6 |
| 7 | 1.419 | 100 | 36.4 | 35.7 | 63.9 |

EXAMPLE 3

Preparation of a conjugate of a Fab fragment of a polyclonal anti-insulin antibody with a human Fc-γ fragment.

From the polyclonal antibody, prepared in the manner described in Federal Republic of Germany Patent Specification No. 27 44 835, there was split off a Fab fragment, a thiol group was introduced and, as also described in Example 1, coupled with an Fcε fragment of human IgG. The methods for antibody cleavage, activation and coupling are described by P. Tijssen in Practice and Theory of Enzyme immunoassay (1985), pub. Elsevier, Amsterdam.

EXAMPLE 4

This example shows the use of a control, which is a conjugate of an Fab fragment of a guinea pig polyclonal antibody against insulin and a human Fcγ fragment, in determination of insulin specific antibodies.

The antibody determination was carried out in the manner described in Example 2. The results obtained are given in the following Table III.

TABLE III

| | substrate reaction time (min.) | | | | | |
|---|---|---|---|---|---|---|
| | 20 | | 40 | | 60 | |
| sample | ΔE | % | ΔE | % | ΔE | % |
| PAB <insulin>-MS-Fab-H-Fcγ | 0.388 | 100 | 0.672 | 100 | 0.918 | 100 |
| Serum 1 | 0.052 | 13.4 | 0.092 | 13.7 | 0.126 | 13.7 |
| Serum 2 | 0.097 | 25.0 | 0.168 | 25.0 | 0.231 | 25.2 |
| Serum 3 | 0.254 | 65.5 | 0.437 | 65.0 | 0.595 | 64.8 |
| Serum 4 | 0.378 | 97.4 | 0.657 | 97.8 | 0.894 | 97.4 |

It can be seen that the samples are in constant relationship to the function control at all three measured times of the substrate reaction. Thus, the measurement time can be freely chosen.

EXAMPLE 5

Preparation of a conjugate of polyclonal antibody against human erythropoietin (EPO) and human immunoglobulin, as well as the determination of EPO antibodies.

White New Zealand rabbits were immunized with 50 ug human EPO and then post-inoculated on the 7th, 14th and 30th day and then every 30th day after the first immunization, in each case with 25 μg of antigen per animal. In addition, complete Freund's adjuvant was always given. From the serum of the animals, IgG was purified by means of ammonium sulphate precipitation and ion exchange chromatography. The animal IgG was subsequently coupled to human IgG in the manner described in Example 1. The conjugate obtained served as a control reagent for the determination of human EPO antibodies.

The carrying out of the antibody determination took place as described in Example 2, except that the microtitre plates were coated with 1.25 μg EPO/ml.

Here, too, as can be seen from the following Table IV, there was obtained a constant quotient of the measurement signals of sample and control reagent so that the color development can be measured and evaluated at any desired point of time between the 15th and 60th minute after commencement of the substrate reaction.

TABLE IV

| | substrate reaction time (min.) | | | | | | | |
|---|---|---|---|---|---|---|---|---|
| | 15 | | 30 | | 45 | | 60 | |
| sample | ΔE | % | ΔE | % | ΔE | % | ΔE | % |
| PAB <EPO> KanIgG-HIgG | 0.354 | 100 | 0.632 | 100 | 0.848 | 100 | 0.975 | 100 |
| sample 1 | 0.049 | 13.8 | 0.085 | 13.4 | 0.111 | 13.1 | 0.128 | 13.1 |
| sample 2 | 0.085 | 24.0 | 0.151 | 23.9 | 0.201 | 23.7 | 0.230 | 23.6 |
| sample 3 | 0.120 | 33.9 | 0.214 | 33.9 | 0.284 | 33.5 | 0.328 | 33.6 |
| sample 4 | 0.166 | 46.9 | 0.298 | 47.2 | 0.392 | 46.2 | 0.450 | 46.2 |

It will be understood that the specification and examples are illustrative but do not limit of the present invention and that other embodiments within the spirit and scope of the invention will suggest themselves to those skilled in the art.

We claim:

1. In a method for determining an antibody in a sample of body fluid wherein said sample is incubated with two receptors $R_1$ and $R_2$, wherein $R_1$ has an antigenic determinant which binds to said antibody to be determined and $R_2$ is labelled with a label which gives a detectable signal so as to form (i) a complex of label and bound antibody and (ii) uncomplexed label, and measuring label in said complex or uncomplexed label as a measurement of said antibody, the improvement comprising comparing said measurement to a control measurement obtained by incubating $R_1$ and $R_2$ with a conjugate of (i) a non-human antibody, an Fab fragment of said non-human antibody of an F(ab')$_2$ fragment of said non-human antibody and (ii) a human immunoglobulin or an Fc portion of said human immuno-globulin, wherein said non-human antibody, Fab, or F(ab')$_2$ fragment binds to the same receptor as the antibody to be determined and measuring complexed or uncomplexed label, and comparing said control measurement to said sample measurement as a measure of antibody in said sample.

2. Method of claim 1, wherein said non-human antibody is a monoclonal antibody.

3. Method of claim 1, wherein said non-human antibody is a rat or mouse monoclonal antibody.

4. Method of claim 1, wherein said sample contains an auto-antibody.

5. Method of claim 1, wherein said sample contains an antibody against a drug administered to a host from which said sample is obtained.

6. Method of claim 1, wherein said sample contains an antibody produced in an allergic response.

7. Method of claim 1, wherein said sample contains auto-antibodies to insulin.

8. Method of claim 1, wherein said sample contains antibodies to islet cells.

9. Method of claim 1, wherein said sample contains antibodies to hepatitis.

10. Method of claim 1, wherein said sample contains antibodies to erythropoietin.

11. Method of claim 1, wherein said sample contains antibodies to plasminogen activator.

12. Method of claim 1, wherein said sample contains antibodies to human immunodeficiency viruses.

13. Reagent for determining an antibody in a sample of a human body fluid, comprising a conjugate containing non-human antibody, Fab or F(ab')$_2$ fragment which binds with a receptor to which said human body fluid antibody binds, said non-human antibody conjugated to a human immunoglobulin or Fc portion thereof, and a receptor $R_s$ to which said conjugate binds and which contains an antigenic determinant which specifically binds with the human body fluid antibody to be determined.

14. Reagent of claim 13, wherein said non-human antibody Fab or F(ab')$_2$ fragment binds to insulin.

* * * * *